(12) United States Patent
Pease, III et al.

(10) Patent No.: US 9,790,459 B2
(45) Date of Patent: Oct. 17, 2017

(54) PERIODIC SYMMETRY DEFINED BIOREACTOR

(71) Applicant: University of Utah Research Foundation, Salt Lake City, UT (US)

(72) Inventors: Leonard Franklin Pease, III, Salt Lake City, UT (US); Swomitra K. Mohanty, Salt Lake City, UT (US); John McLeenan, Salt Lake City, UT (US); Tony Butterfield, Salt Lake City, UT (US); Tyler Lee, Salt Lake City, UT (US); Samuel Doane, Salt Lake City, UT (US); Rete Browning, Salt Lake City, UT (US); Yen-Hsun Tseng, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 110 days.

(21) Appl. No.: 14/625,470

(22) Filed: Feb. 18, 2015

(65) Prior Publication Data
US 2015/0299633 A1 Oct. 22, 2015

Related U.S. Application Data

(60) Provisional application No. 61/941,280, filed on Feb. 18, 2014.

(51) Int. Cl.
*C12M 1/00* (2006.01)
*C12N 1/12* (2006.01)
(Continued)

(52) U.S. Cl.
CPC ............ *C12M 23/34* (2013.01); *C12M 23/44* (2013.01); *C12M 27/20* (2013.01); *C12M 29/06* (2013.01);
(Continued)

(58) Field of Classification Search
CPC ...... C12M 21/02; C12M 23/18; C12M 23/22; C12M 23/34; C12M 23/44; C12M 23/58; C12M 29/06; C12M 29/18
See application file for complete search history.

(56) References Cited

U.S. PATENT DOCUMENTS 5,641,462 A * 6/1997 Sohn .................. B01D 11/0469
                                              210/151
5,863,119 A   1/1999 Yergovich et al.
(Continued)

FOREIGN PATENT DOCUMENTS

WO   WO 2013/095300   6/2013

OTHER PUBLICATIONS

Poreh et al.; "Investigation of a Turbulent Radial Wall Jet." Journal of Applied Mechanics, vol. 34, No. 2; Jun. 1967; pp. 457-463.
(Continued)

*Primary Examiner* — William H Beisner
(74) *Attorney, Agent, or Firm* — Thorpe North & Western, LLP

(57) ABSTRACT

A bioreactor can include a plurality of unit cells. Each unit cell can include a floor configured to support a volume of liquid, the floor being symmetric across at least one axis of symmetry, and an injection port oriented at a center point of at least one axis of symmetry and configured to inject a fluid into the volume of liquid. The bioreactor can also include a peripheral side wall surrounding the plurality of unit cells such that the volume of liquid is retained in the bioreactor.

17 Claims, 10 Drawing Sheets

(51) Int. Cl.
    *C12M 1/26*     (2006.01)
    *C12M 3/00*     (2006.01)
    *C12M 1/34*     (2006.01)
    *C12N 1/20*     (2006.01)

(52) U.S. Cl.
    CPC ............ *C12M 33/04* (2013.01); *C12M 41/00* (2013.01); *C12N 1/12* (2013.01); *C12N 1/20* (2013.01)

(56) References Cited

U.S. PATENT DOCUMENTS

| | | |
|---|---|---|
| 7,718,065 B2 | 5/2010 | Jordan |
| 7,951,555 B2 | 5/2011 | Taylor et al. |
| 8,409,852 B2 | 4/2013 | Redford |
| 8,636,402 B2 | 1/2014 | Medoff et al. |
| 2010/0260618 A1 | 10/2010 | Parsheh et al. |
| 2010/0325948 A1 | 12/2010 | Parsheh et al. |
| 2011/0287541 A1 | 11/2011 | Cuello et al. |
| 2013/0309771 A1 | 11/2013 | Gevaert et al. |

OTHER PUBLICATIONS

Supramaniam et al.; "Study on the pH Changes of Microalgae (*Tetraselmis chuii*) Cultivated in Newly Developed Closed Photobioreactor using Natural Sunlight and Artificial Light;" Journal of Energy & Environment (2012), vol. 4, No. 1; pp. 18-20.

\* cited by examiner

U.S. 9,790,459 B2

PERIODIC SYMMETRY DEFINED BIOREACTOR

RELATED APPLICATIONS

This application claims priority to U.S. Provisional Application No. 61/941,280 filed on Feb. 18, 2014, which is incorporated herein by reference.

BACKGROUND

Although photosynthetic microorganisms (e.g., microalgae, yeast, bacteria, etc.) have been investigated extensively over past decades, critical engineering challenges remain that limit the economic viability of transportation fuel production from these sources. First, state-of-the-art reactors for cultivating or exploiting these organisms remain difficult to scale up from laboratory or similar scale proof-of-concept facilities. Consider algae growth, for example. Large, stagnant pools are readily scalable (with simply more acreage) but do not provide sufficient circulation for optimal growth environments. Many methods use paddlewheel driven raceways to circulate the microorganisms. However, raceways are inherently limited in their scalability, have moving parts, and are significantly more expensive than open ponds. Secondly, again considering algae as an example, harvesting methodologies can require the algae to be completely dried before extraction of algal oils with hexane. The drying steps can be energy extensive and hexane may extract only about a third of available algal oils. The lack of efficient and scalable bioreactor designs and inefficient harvesting methods prevents phototropic microbes or similar agents from making a significant contribution to the U.S. energy supply and manufacturing.

SUMMARY

Accordingly, a bioreactor can include a plurality of unit cells. Each unit cell can include a floor configured to support a volume of liquid, the floor being symmetric across at least one axis of symmetry, and can include an injection port oriented at a center point of the at least one axis of symmetry and configured to inject a fluid into the volume of liquid. Typically, the fluid can be injected from a top or a bottom of the volume of liquid along the axis of symmetry. The bioreactor can also include a peripheral side wall surrounding the plurality of unit cells such that the volume of liquid is retained in the bioreactor substantially free of internal walls.

Figure 1:
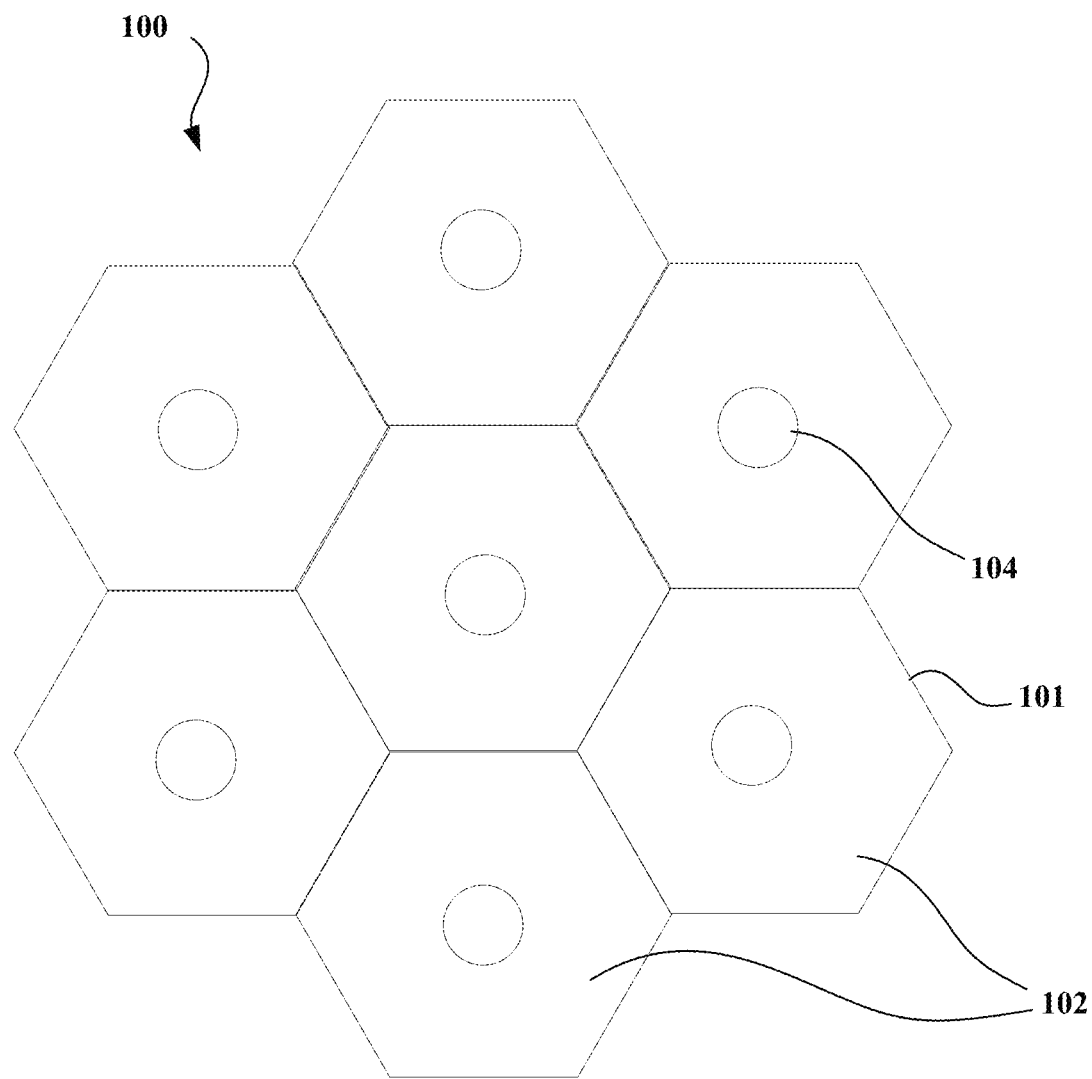
FIG. 1 is shows a top plan view of a bioreactor having seven hexagonal unit cells in accordance with one example of the present technology.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

It is noted that, as used in this specification and in the appended claims, the singular forms "a," "an," and "the" include plural referents unless the context clearly dictates otherwise. Thus, for example, reference to "a layer" includes one or more of such features, reference to "a nozzle" includes reference to one or more of such devices, and reference to "processing" includes reference to one or more of such steps.

As used herein, the terms "about" and "approximately" are used to provide flexibility, such as to indicate, for example, that a given value in a numerical range endpoint may be "a little above" or "a little below" the endpoint. The degree of flexibility for a particular variable can be readily determined by one skilled in the art based on the context.

As used herein, the term "substantially" refers to the complete or nearly complete extent or degree of an action, characteristic, property, state, structure, item, or result. The exact allowable degree of deviation from absolute completeness may in some cases depend on the specific context. However, the nearness of completion will generally be so as to have the same overall result as if absolute and total completion were obtained. The use of "substantially" is equally applicable when used in a negative connotation to refer to the complete or near complete lack of an action, characteristic, property, state, structure, item, or result.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Reference will now be made to the exemplary embodiments illustrated, and specific language will be used herein to describe the same. It will nevertheless be understood that no limitation of the scope of the technology is thereby intended. Additional features and advantages of the technology will be apparent from the detailed description which follows, taken in conjunction with the accompanying drawings, which together illustrate, by way of example, features of the technology.

With the general examples set forth in the Summary above, it is noted in the present disclosure that when describing the system, or the related devices or methods, individual or separate descriptions are considered applicable to one other, whether or not explicitly discussed in the context of a particular example or embodiment. For example, in discussing a device per se, other device, system, and/or method embodiments are also included in such discussions, and vice versa. Furthermore, various modifications and combinations can be derived from the present disclosure and illustrations, and as such, the following description should not be considered limiting.

Reactor Design

Emerging alternative energy technologies are available for electricity production, but the options for liquid transportation fuels that have high energy density, can be transported safely, and do not compete with food production resources (arable land, water, etc.) remain limited. One promising option is microalgae because they directly produce hydrocarbon rich materials, utilize $CO_2$, and can be grown in wastewater in a sustainable fashion. Furthermore, production and growth of a wide variety of microorganisms is currently limited due to expense and challenges related to maintaining desired growth conditions throughout a growth volume. The bioreactors described herein can be particularly suitable for microorganisms such as, but not limited to, *E. coli* bacteria for free fatty acid production, dairy yeasts for probiotoics, lactic acid bacteria, microalgae, cyanobacteria, enzyme production, bacterial sewage treatment, etc. These bioreactors can also be suitable for both heterotrophic and autotrophic organisms.

The present technology provides bioreactor units optimized for, among other parameters, low nutrient levels and wastewater streams such as water from mining and industrial processes. From the perspective of microalgae, the bioreactors allow sufficient light penetration and circulation to provide light for the microorganism to grow, and provides efficient circulation to efficiently deliver nutrients to the microorganism, thereby allowing for more efficient microorganism cultivation. In the case of algae, these bioreactors can allow for increased and maximum lipid output for biofuel production.

Figure 2:
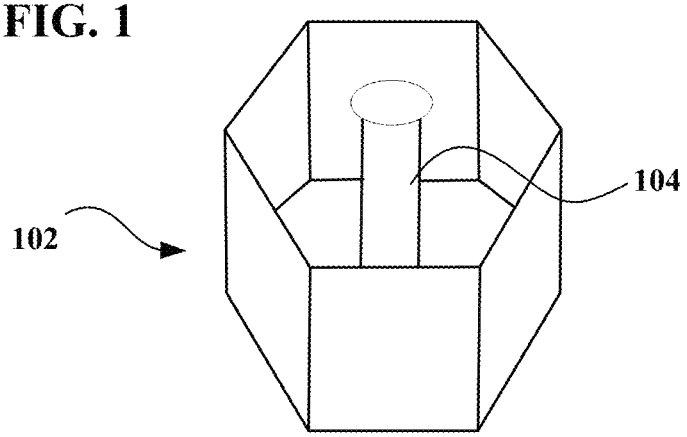
FIG. 2 shows a perspective angle view of a hexagonal unit cell of a bioreactor unit with a peripheral side wall in accordance with one example of the present technology.
Figure 3:
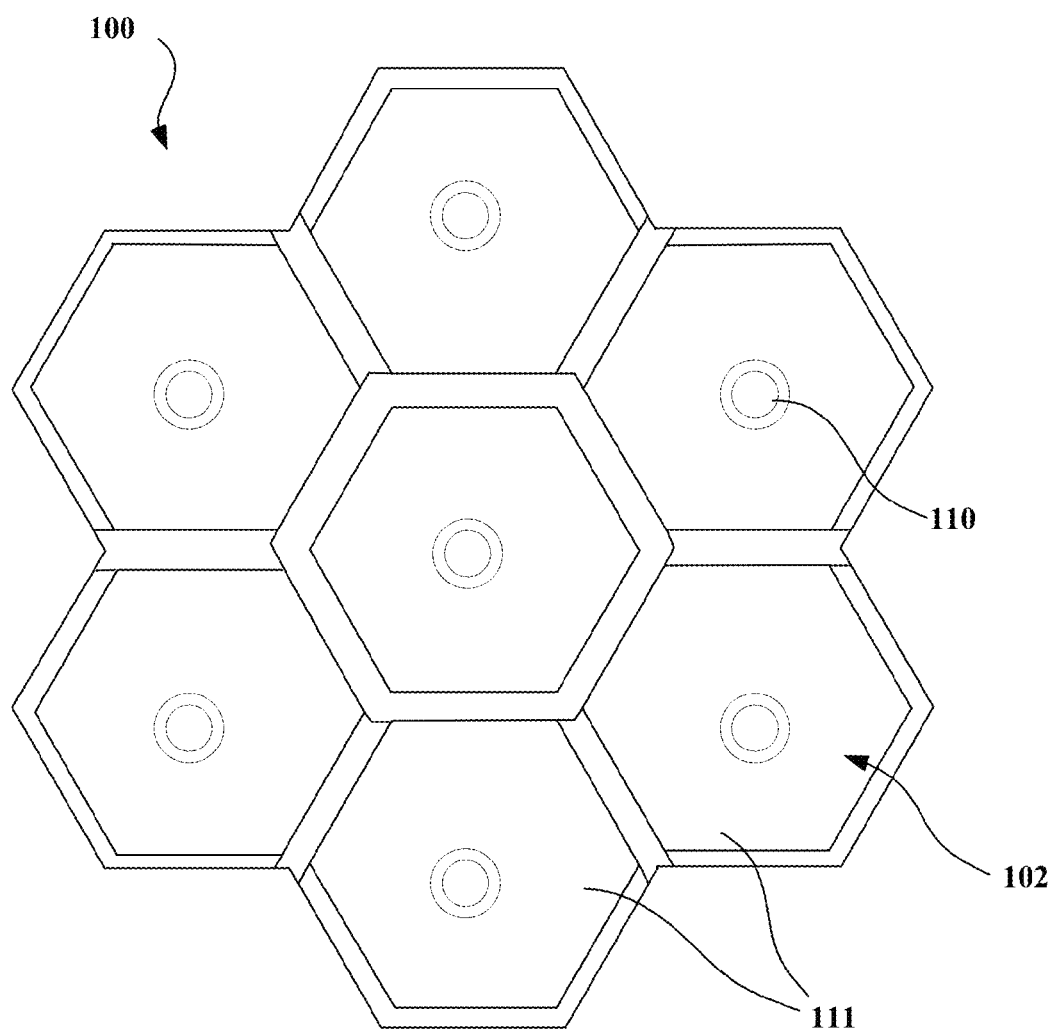
FIG. 3 shows a bottom plan view of a bioreactor having seven hexagonal unit cells in accordance with one example of the present technology.

The bioreactor is a periodic symmetry based unit which can be readily sized and optimized using fluid dynamics rather than physical walls to define multiple reactor cells within a larger composite bioreactor. More specifically, unit cells can be defined hydrodynamically. Referring to FIG. 1, an exemplary design of a bioreactor 100 includes a plurality of symmetric unit cells 102. The interior unit cells 102 typically do not include interior walls so as to minimize dead spaces throughout fluid within the bioreactor 100. The bioreactor 100 comprises hydrodynamically defined unit volumes that allow for improved mass transport and vertical mixing. Individual unit cells 102 can include a nozzle assembly 104 that recirculates the fluid, nutrients, and microorganisms within the unit cell. The nozzle can be placed and configured as further described in more detail below. The exterior unit cells include portions of the peripheral side wall 101. In this manner, a massively parallel bioreactor design employs strategic placement of nozzles or injection ports. The term nozzle is intended to include any opening which allows delivery of fluid and can include fluid outlet shaping nozzles and simple conduit openings (e.g. open pipe). FIG. 2 illustrates a hexagonal unit cell 102 which can be incorporated into a composite bioreactor assembly as a repeating array of unit cells. The peripheral side wall shown in FIG. 2 surrounds the unit cell; however, individual unit cells are not generally completely enclosed when used as part of the bioreactor unit. The dimensions of these unit cells can be optimized to maximize microorganism growth, minimize light gradients, and provide optimal delivery of $CO_2$ and other nutrients. Factors that can be utilized for optimization include flow rate out of the nozzles, position of the nozzles, light penetration through the cell, and heat and mass transport that can be optimized depending on the microorganism species. In the case of algae, optimizing nutrient distribution can also accelerate the growth of microorganisms.

Figure 4:
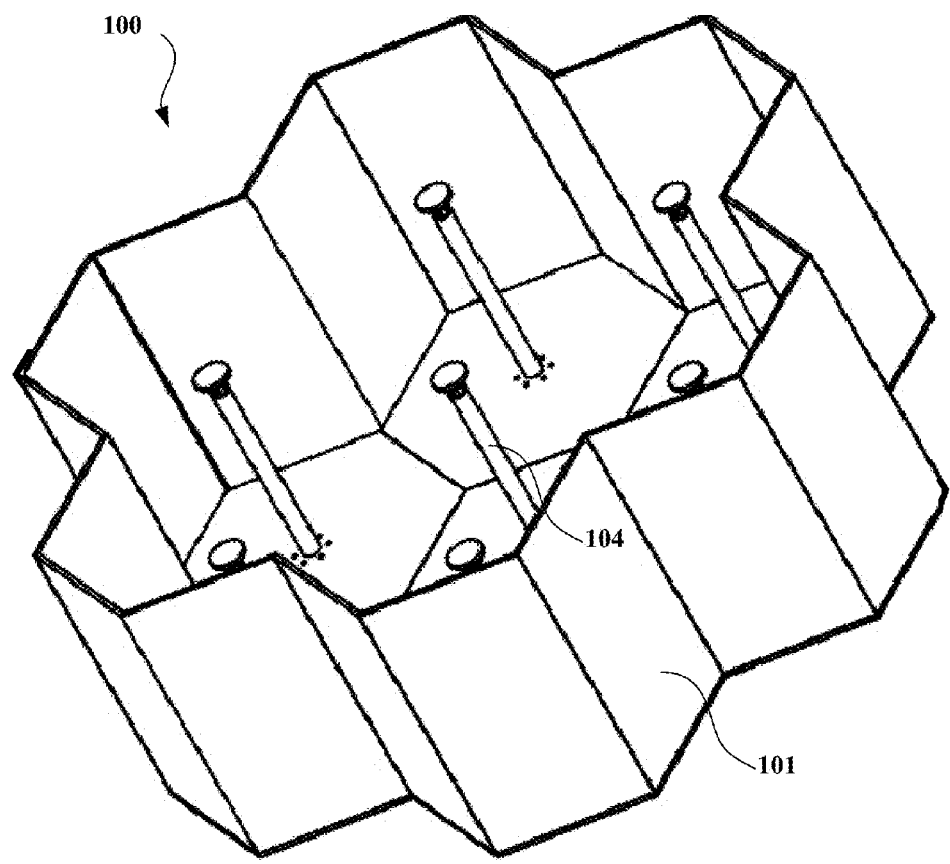
FIG. 4 shows a Dutch angle view of a bioreactor having seven hexagonal unit cells in accordance with one example of the present technology.

FIG. 4 shows a bottom view of the same unit as in FIG. 1, having a plurality of floor segments 111 which are connected together. However, a single integral floor piece can also be used. Thus, the floor of the bioreactor can be a continuous floor piece shared by multiple unit cells, and in some cases all of the plurality of unit cells, or it can be made up of unit floor pieces corresponding to a single unit cell. For example, hexagonal floor pieces can be assembled into a large bioreactor, with one floor piece for each unit cell. Floor pieces can have self-sealing junctions, humidity sensor locations, built-in flow nozzles, pumps, and any other equipment necessary for operation. In other examples, a floor piece can include multiple unit cells such as seven hexagonal unit cells, and the floor piece can be shaped to be tessellated with additional floor pieces. Floor pieces can also be in other shapes to correspond to the shapes of unit cells, such as rectangles, squares, or triangles. Floor pieces can be formed of any suitable material which provides structural integrity and fluid containment. Non-limiting examples of suitable floor materials can include geomembranes (e.g. for large scale applications), opaque or transparent polymer panels, and the like.

Floor pieces can be optionally coated with a non-stick coating to prevent algae from sticking to the surface of the floor. For example, the coating can be a hydrophobic silane. The coating can be performed, for example, by NaOH etching or plasma treatment followed by dip coating. Other coatings can also be used to minimize adherence of algae or other materials. Non-limiting examples of floor coatings can include surfactants, lipid coatings, biofilms, and the like. In one aspect, the floor of the bioreactor can be placed on a raised surface such as a table or a platform in order to allow for rapid leak detection and access to pumps, piping, inlet manifolds and other equipment. Alternatively, conduits, nozzle assemblies and the like can be oriented above the volume of fluid to provide accessibility to equipment for repair and maintenance.

A plurality of hexagonal unit cells 102 or other symmetrically shaped unit cells can each include a dedicated nozzle assembly 104. The array of unit cells can be joined with one another to form a bioreactor unit 100 as illustrated in FIG. 1 which is a seven unit cell bioreactor unit which is also show in FIG. 4 as a Dutch angle view showing nozzle assemblies 104. Hydrodynamic fluid flows are created within the individual unit cells of the bioreactor using fluid jets, injection pumps, injection ports, or other circulation units. In one embodiment, fluid (including nutrients and the microorganisms) follows the fluid jet vertically from its nozzle to the photobioreactor surface. The fluid then moves along the upper surface until it approaches a midpoint between two adjacent nozzles where continuity forces the fluid down and then along the bottom of the reactors to complete the recirculation cycle of the unit cell. Alternatively, in another embodiment, fluid can be injected to the bottom of a unit cell, which causes an opposite flow direction. For example, within a unit cell, fluid (including nutrients and the microorganism(s) or similar) leaves the nozzle (e.g. in a radially dispersed pattern) with downward flow and spreads out along the floor of the reactor unit until it approaches a midpoint between two adjacent nozzles where continuity forces the fluid up and then along the top of the unit to complete a recirculation cycle in the unit cell.

Periodically positioning the nozzles and/or injection ports generates an array of unit cells. The individual unit cells lack internal walls or barriers that would increase friction and raise operating and capital costs. Additionally, eliminating the internal barriers prevents microorganism buildup along the internal wall/barriers. Because each unit cell is effectively independent from its neighbor at steady state (similar to the convective Bénard cells of the thermally driven Rayleigh-Bénard instability), the system is readily scalable to a semi-infinite number of unit cells that are defined by symmetry and not by material walls. These arrays can cover the available footprint as desired, simply by nozzle placement within a pool. Photobioreactors comprised of periodic fluid dynamically driven recirculation zones (i.e. unit cells) can grow photosynthetic algae in a highly scalable manner. In one alternative, temporary removable partitions can be inserted in order to isolate regions of the liquid volume to facilitate cleaning, maintenance, etc. For example, a removable partition assembly can be lowered into the volume of fluid in order to isolate a portion of the fluid and associated region of the bioreactor. The isolated fluid can then be removed or treated, and then the partition assembly can be removed.

Figure 5:
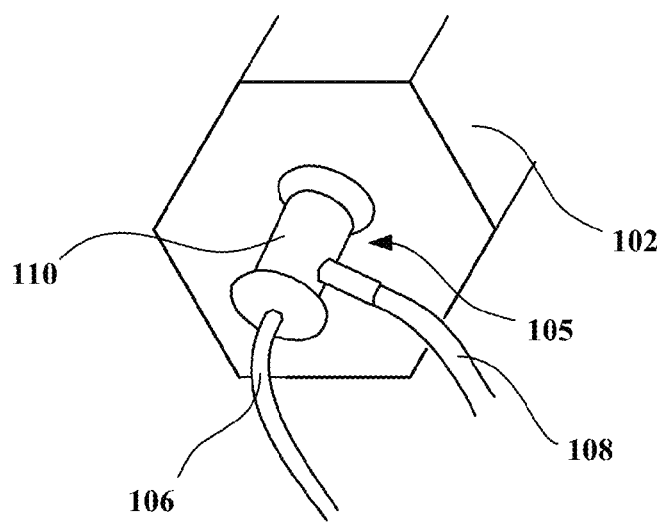
FIG. 5 shows a Dutch angle view of the bottom of a hexagonal unit cell of the bioreactor unit, including a fluid intake and injection port lines that lead to a pump in accordance with one example of the present technology.

A fluid intake can be positioned adjacent to the base of the injection nozzle, although other locations could be used. Alternatively, the fluid outlet can optionally be an array of holes drilled in the floor. Fluid can flow through the fluid intake to a fluid line leading to a pump, where the fluid is recirculated back to the injection nozzle. The flow lines and pump can be underneath the floor. The fluid intakes may also be introduced from above the unit cells far above the floor. As illustrated in FIG. 5, the bioreactor unit can have a fluid circulation assembly 105 which introduces and withdraws fluid from the nozzle assembly 104. A fluid intake 106 can introduce (or withdraw) fluid from a central portion of the nozzle assembly. Fluid injection lines 108 can be fluidly coupled to outlet holes 116 through the fluid circulation assembly. An injection stub 110 can provide a central connection housing for each of the intake and injection lines. Further, the fluid circulation assembly can be located at a bottom underside surface of the individual unit cells 102. The fluid intake and fluid injection lines can be fluidly connected to a pump, not shown, that provides a circulatory force for recirculation within each of the unit cells. As the fluid returns to the cell, the nozzle assembly distributes the fluid so as to generate desired circulatory flows.

Figure 6:
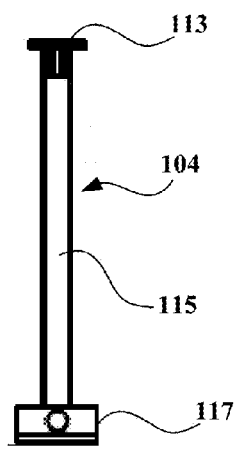
FIGS. 6-8 show different views of a nozzle and circulation control assembly in accordance with one example of the present technology.
Figure 7:
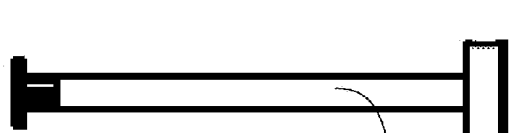
Figure 8:
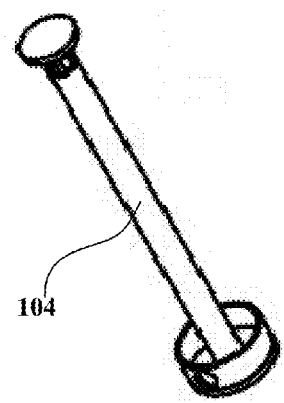

FIGS. 6-8 display differing views of the nozzle assembly 104 that can be used in connection with each unit cell. Fluid flows are designed to radiate out from the nozzle in each individual unit cell along a horizontal axis, then pass vertically through the unit cell before circling back towards the nozzle assembly at a collection port or ports. In FIG. 6, the nozzle assembly is shown having a distribution cap 113 at a distal end of a riser 115. A base portion 117 can be connected at an opposite end of the riser and can include collection ports which are fluidly connected to fluid injection lines 108 (FIG. 5). The base portion can be secured to the bioreactor at a periodically symmetric location.

Strategic placement of nozzles or injection ports can create the symmetric unit cells. In one example, within a unit cell, fluid follows the fluid jets vertically from its nozzle to the pool surface. Fluid then moves along the upper surface until it approaches the midpoint between two nozzles where continuity forces the fluid down and then along the bottom of the reactors to complete the recirculation cycle of the unit cell. In another example, fluid flow can be reversed. Regardless, periodically positioning the nozzles generates an array of unit cells without internal walls or barriers that would increase friction and raise operating and capital costs. The nozzle height can be placed to achieve optimal flow of the fluid so that all of the algae is recirculated near the surface of the fluid to receive sunlight. In some examples, the nozzle can have a fluid outlet oriented at a nozzle height of 0.2% to 99.8% of a wall height of the peripheral side wall. In examples where the surface of the liquid is below the wall height of the peripheral side wall, the nozzle height can be 0.2% to 99.8% of the height of the liquid surface. In one example, the nozzle height can be from 0.2% to 10% of the height of the liquid surface. Typically, the total vertical height of the liquid pool will not exceed 40 feet. The nozzles are most often within a few inches of the floor in each case which facilitates sweeping settled algae up so that it can access the light available at the top of the reactor.

Figure 9:
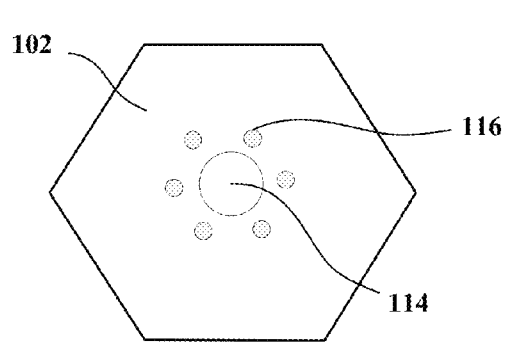
FIG. 9 shows a top plan view of a hexagonal unit cell of a bioreactor unit without the nozzle; this view displays a centrally located hole that houses the nozzle and six intake points equally distance spaced apart from one another in accordance with one example of the present technology.
Figure 10:
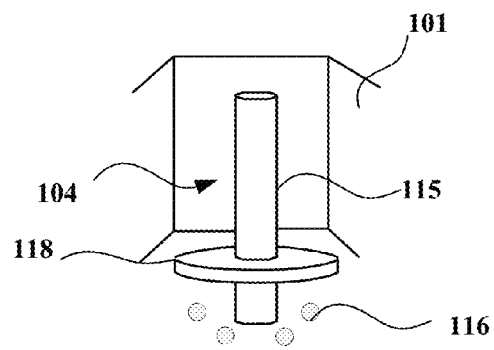
FIG. 10 shows a horizontal view of a hexagonal unit cell including a nozzle, four injection points, and a flow guard, in accordance with one example of the present technology.

As illustrated in FIGS. 9 and 10, the nozzle assembly 104 can be secured to a centrally located diameter hole 114 oriented within a floor of a unit cell 102. Although other configurations can be suitable, six fluid outlet holes 116 can be oriented equidistance from each other circumferentially about the central hole 114. However, these outlet holes can be drilled in each unit cell to allow for flexible placement of flow sources and sinks, as shown in FIGS. 9 and 10.

Figure 11:
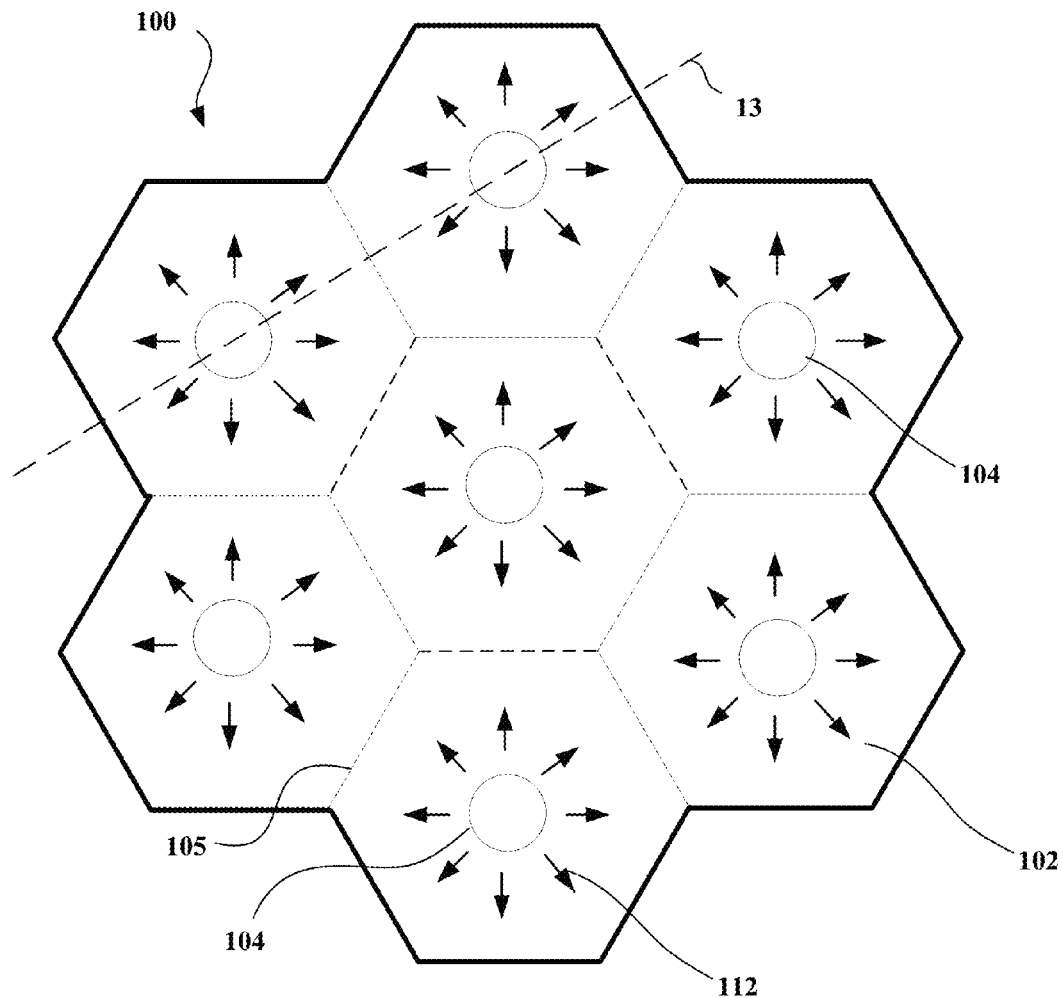
FIG. 11 shows a top plan view of a bioreactor design, with flow recirculation areas shown as arrows in the bioreactor unit having seven hexagonal unit cells in accordance with one example of the present technology.
Figure 12:
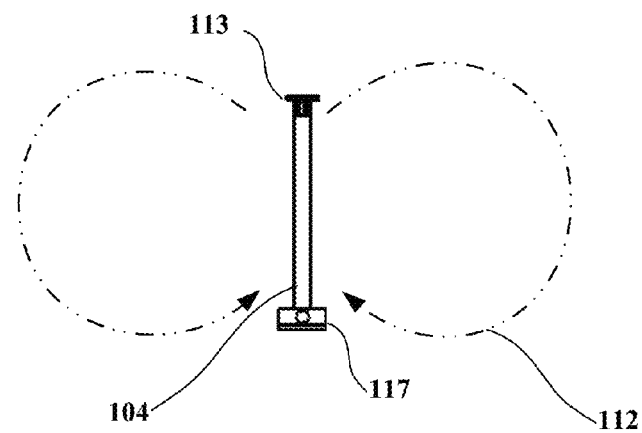
FIG. 12 shows a side view of a nozzle used in a unit cell with flow recirculation lines displaying the vertical flow within a unit cell in accordance with one example of the present technology.
Figure 13A:
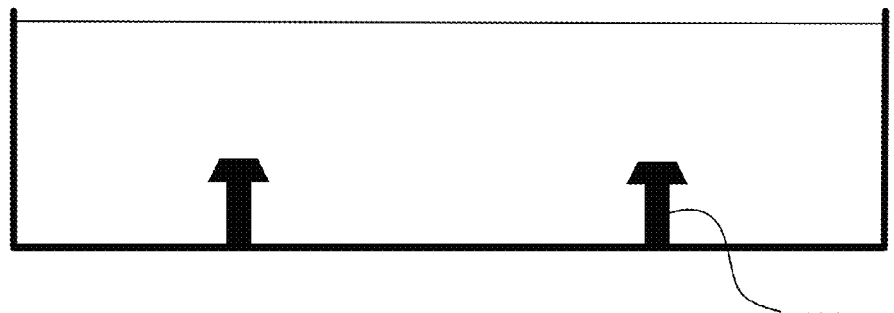
FIG. 13A is a side cross-sectional view of FIG. 11 at stagnant conditions.
Figure 13B:
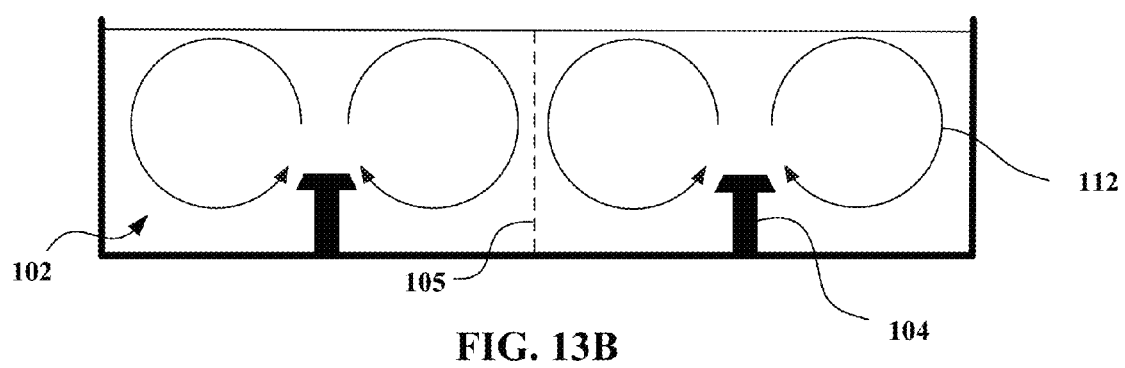
FIG. 13B is a side cross-sectional view of FIG. 11 at circulation conditions defining unit cells in accordance with one example of the present technology.

A deflection baffle can be oriented about the base of the injection nozzle and spaced from the floor, such that the fluid intake is obscured by the deflection baffle when viewed from an aerial top view. The deflection baffle can be a disc that covers the fluid intake. Alternatively, fluid flow can be injected at the array of holes or adjacent to the floor and the intake can be oriented at a desired intake height. In this case, the flow travels laterally outward along the floor of the unit cell. Further, the baffles can prevent the flow from taking a very short path from the injection to uptake points without circulating through the body of the unit cell. In one aspect, the nozzle assembly can optionally include a disk 118 as the deflection baffle that can be secured along the riser 115 above the unit cell base to direct flow vertically or horizontally along the unit cell base. The disk can be any suitable material which allows for deflection and redirection of fluid horizontally along the reactor floor. FIG. 11 illustrates fluid flows 112 within an individual unit cell which are emanating outwardly. FIG. 12 shows as side view of circulating fluid flow 112. In this case, fluid is injected into the unit cell via distribution cap 113 and follows a generally circulating pattern back toward the base portion 117. Accordingly, as illustrated in FIG. 13A, before circulation begins within the bioreactor, the volume of fluid is stagnant. Once fluid flow begins as illustrated in FIG. 13B, circulation zones hydrodynamically define the unit cells 102 such that virtual flow walls 105 are formed between adjacent unit cells.

Figure 14:
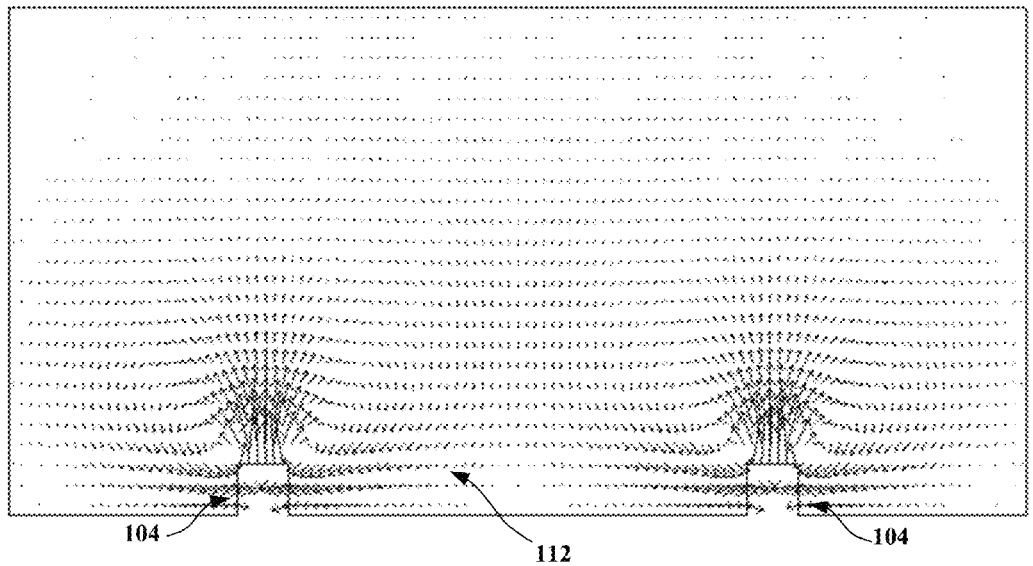
FIG. 14 shows a flow simulation profile in a bioreactor unit having two jet nozzles in accordance with one example of present technology.
Figure 15:
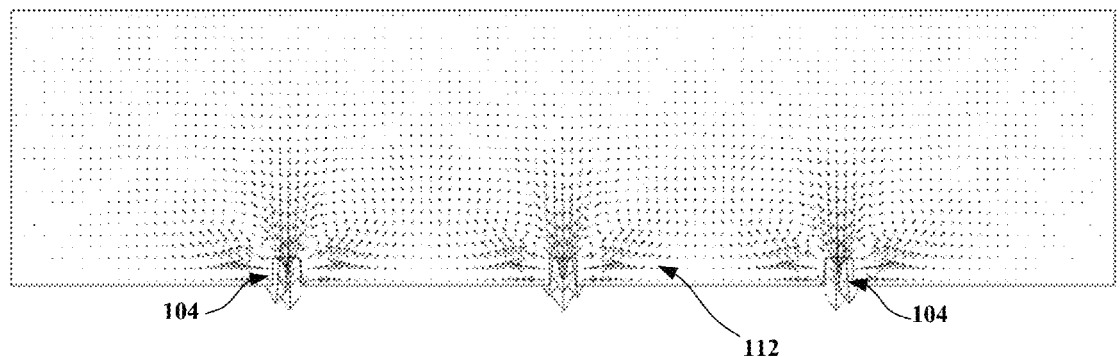
FIG. 15 is a flow profile in a bioreactor having three jet nozzles with in a downward direction relative to a top of the flow control assembly according to the present technology.

Consistent with these principles, FIG. 14 provides a simulated velocity flow profile where flow injection occurs at a tip of the nozzle assembly, while FIG. 15 is a simulation velocity profile showing a reverse flow.

Figure 16:
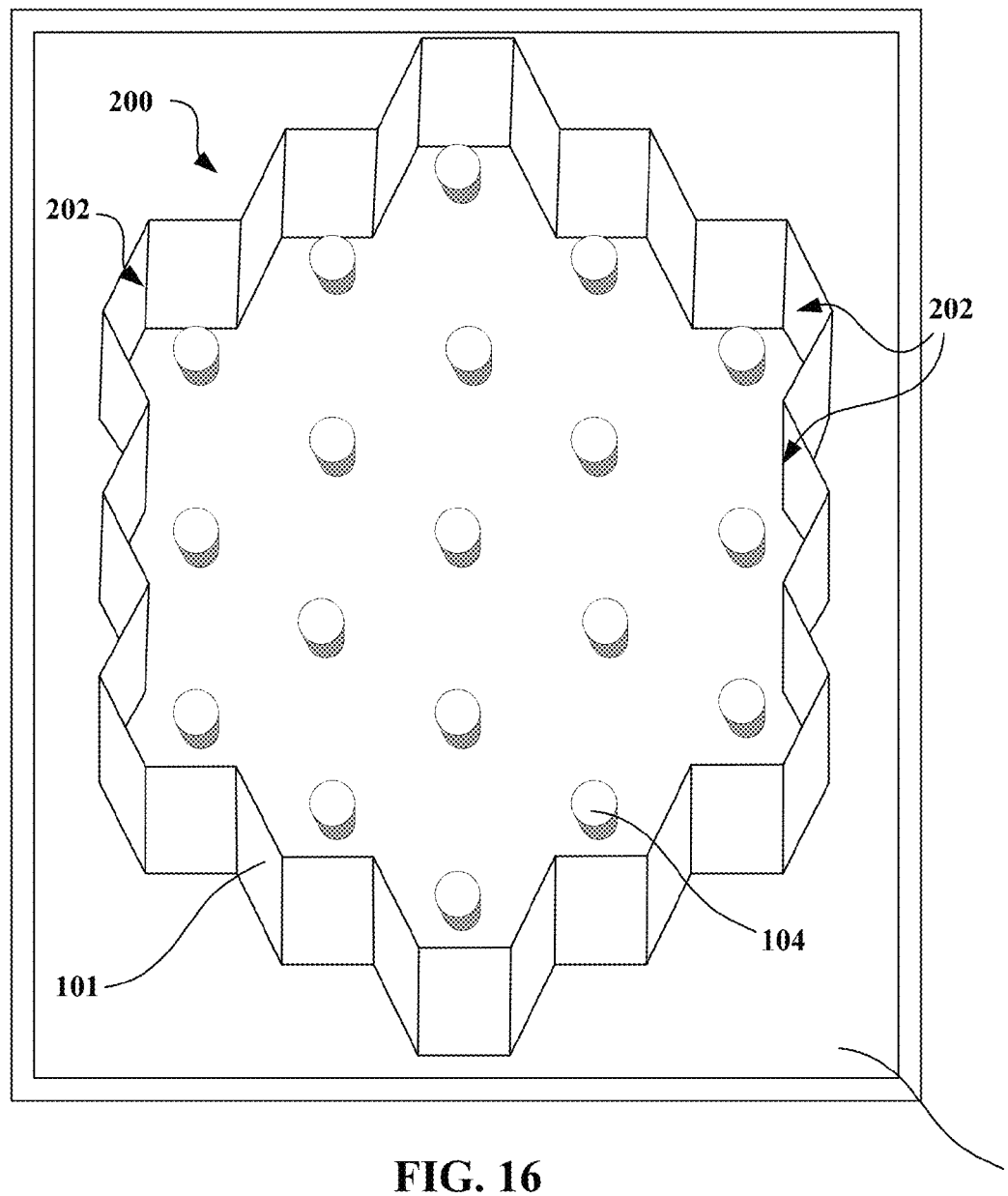
FIG. 16 shows a top perspective view of a bioreactor design having nineteen hexagonal unit cells and placed on top of an elevating surface in accordance with one example of the present technology.
Figure 17:
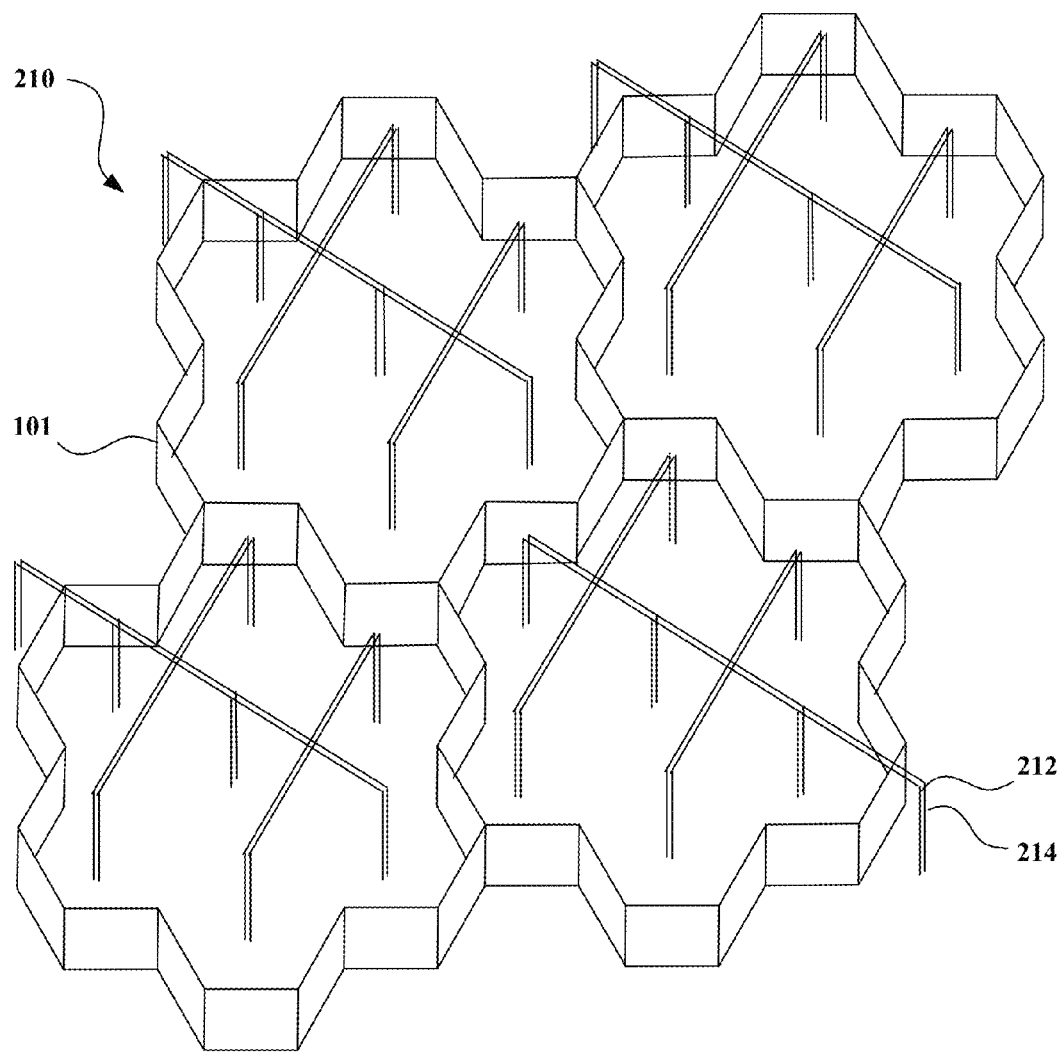
FIG. 17 shows a Dutch angle view of four bioreactor units each having seven hexagonal cells wherein the connection lines leading to the pump are configured at the top of the bioreactor in accordance with one example of the present technology.

As described previously, the bioreactor unit is highly scalable and can include a variety of unit cells in number and shape. Reactors can have a varying number of unit cells. The quantity of unit cells can be semi-infinite. In one embodiment, including hexagonal unit cells, the bioreactor can have 1, 7, 19, 37, 61 or other numbers of unit cells, with fluid manifolds feeding each unit cell. The quantity of unit cells will vary based on the symmetric shape and size of the individual cells and the area where the bioreactor is being placed. FIG. 16 shows a top view of a bioreactor 200 having nineteen hexagonal unit cells 202. The bioreactor can be raised above the ground and placed on an elevated surface 204. The use of an elevated surface allows for an individual to easily locate and repair a leak or otherwise access ports, lines, heaters, sensors, and other equipment. For example, heaters or coolers can be oriented along flow lines or otherwise in thermal communication with the fluid to control temperature conditions within the bioreactor. Sensors can also be oriented in one or more locations within the bioreactor to monitor temperature, heat, oxygen content, nitrate/phosphate levels, uniformity, turbidity, etc. In another alternative embodiment, as shown in FIG. 17 the bioreactor unit 210 can include a injection port assembly 212 that distributes fluid along pump connection lines and injection ports which run from pumps along a top of the bioreactor. A distribution location of the injection port can be oriented as with previously discussed configurations in order to form desired recirculating flow patterns. Notably, the injection port assembly 212 can operate in parallel with a complimentary collection port assembly 214. Specifically, the collection port assembly can be oriented to collect a portion of circulating fluid and direct the fluid to a pump which redirects fluid back through the injection port assembly. While these figures display hexagonally shaped unit cells it is understood that the shape and configuration of the bioreactor unit can be modified as described herein.

Notably, interior unit cells can lack interior walls/borders while outer unit cells include walls only along a peripheral portion of the bioreactor. Thus, these unit cells are hydrodynamically defined rather than structurally defined by physical walls. This allows for the unit cells to be arranged in a manner that minimizes the sidewall area and fluid frictional losses in the bioreactor. Removing the material boundaries between unit cells also decreases pumping costs by reducing wall friction. In addition, removing walls reduces the material costs, minimizes cell attachment expenditures, lowers leaching rates, and substantially eliminates stagnation zones. Furthermore, the outer peripheral walls can align with symmetric unit cells as illustrated in FIGS. 4, 11, 16 and 17. However, in some cases an existing volume such as a pond or other suitable fluid retention volume can be retrofitted as described herein. In such cases, the unit cells are oriented within an existing volume such that perimeter spaces between unit cells and existing peripheral walls can exist. In these perimeter spaces, conditions may not be optimized in the same manner as within unit cells. Nonetheless, such non-ideal conditions may be suitable for some applications and microorganisms.

The bioreactor units can be constructed out of a variety of suitable weather resistant materials. In one embodiment, transparent polycarbonate can be used. Transparent polycarbonate is known to withstand long-term weathering and allow sunlight through the sidewalls. Other suitable translucent materials include, but are not limited to, acrylic, glass, and the like. The bioreactor units can also be constructed out of other durable materials such as steel or concrete with optional coatings to reduce adherence to or undesirable interaction with walls such as those previously described.

Each module can include one or more unit cells, requisite nozzles, piping, and optionally mass flow controllers, leak detectors (humidity sensors), and electrical leads. Self-sealing hinges or bolts with polycarbonate bonder and silicon sealant can be used to form a leak-tight solvent weld to join adjacent modules. The reactors can be assembled on a raised platform to allow for rapid leak identification and repair. Flow to each nozzle can be controlled separately by mass flow controller (with optional fail safe settings) and a process control system so that the operator can tune each unit. For example, nutrients and $CO_2$ can be metered into the volume of fluid under well known schedules based on the particular microorganism. Alternatively, large in-ground installations with overhead nozzles can be used.

Reactor productivity can scale linearly with the number of unit cells. There can be a modest improvements as the number of unit cells increase because the ratio of symmetry-to-material boundaries increases, thereby decreasing internal shear stresses. The fluid flow rates from each nozzle can be uniform and steady. Required pump power can be minimized by using symmetry-defined boundaries instead of material-defined boundaries. The unit cells can be designed to cover the available reactor footprint as desired simply by varying nozzle placement within a pool of nearly any geometry. Thus existing pools can be used by inserting a nozzle assembly within the pool. Volumes which fall outside the unit cells can be non-conforming. Such non-conforming volumes can be accommodated if reactor conditions are not adversely affected, or if inserts can be used to make the peripheral wall conforming with unit cell dimensions. Thus, straight or curved peripheral walls can be made conforming with suitable insert siding that gives the hexagonal structure, for example. Modular construction (e.g., by joining adjacent hexagons or other shaped units) can allow these reactors to be located anywhere from retired shrimping ponds, urban rooftops, farms, and refineries to mines, airbases, and oil fields. Thus, these reactors can range from several centimeters across to multiple acres and are not particularly limited in size.

Bioreactors can be optimally constructed with 7, 19, 37, 61, etc unit cells based on the hexagonal design (=1+6Σn, where n is an integer representing reactor generation) (each ~1 L volume). Other bioreactor configurations can be used, incorporating any symmetrically shaped unit cell. For example, substantially parallel rows of hexagons that do not follow this formula are certainly possible and likely in rectangular ponds. While hexagonally shaped unit cells are specifically highlighted any symmetrical unit cell shape can be used.

In one embodiment, the reactors can be made of clear acrylic plate with adequate thickness for structural integrity, to facilitate flow visualization and allow for light penetration. The use of transparent materials such as acrylic or polycarbonate can allow sunlight to pass through to reactor contents, maximizing growth in the case of algae. Full scale implementations can utilize other materials; for example, steel, concrete, or any other materials that can be used to construct the bioreactor.

Although specific dimensions can vary, one example of a hexagonal system includes, at the center of each hexagon, a 1 inch diameter hole and six ¼ inch holes equidistance from each other and 2 inches from the center can be drilled to allow for flexible placement of flow sources and sinks A 1.5 ft long tube and an optional 3 inch diameter disk can be secured above the reactor base to direct flow vertically or horizontally along the reactor base. A centrifugal pump (e.g. Model OPWG-29) can be used to circulate fluid in the reactor contents at flow rates of 0.5, 1, 3, 6 gal/min/cell. Although a centrifugal pump can be used, any fluid flow mechanism can be suitable if it does not detrimentally affect the reactor contents during pumping. Non-limiting examples of such devices can include disc pumps, screw/auger pumps, piston pump, Moyno pumps (progressive cavity pumps) or other positive displacement devices, or other low-shear pumps, depending on the type of microorganisms. The exact configuration of the flow sources and sinks, as well as the flow rate can vary based on the unit cell shape, the area where the reactor is placed, the microorganism being harvested, or the specific reactor purpose.

Variations of the flow profiles can be achieved. Introducing algae or other microorganisms can distort the flow fields since gravitationally induced settling distorts the concentration profile. Re-suspending settled microorganisms can set a minimum pump power for optimal productivity. Stagnation points can occur between circulation flow profiles, as well as at the floor and surface along the boundaries between unit cells. Various measures can be taken to minimize stagnation points, although settling can in part ameliorate this concern. Such measures can include, but are not limited to, periodically pulsing fluid flow, asymmetric free moving nozzles which vary jet direction based on pressure from fluid ejection, and the like.

Reactor flow can be provided by pumps (such as McMaster-Carr, 4291K55) operated in parallel with an additional pump (and backup generator) on standby to provide continuous circulation. If a nozzle breaks, the process control system can identify locally attenuated flow as new symmetry boundaries tessellate to enclose a larger volume. An isolation chamber the same size as a unit cell but with an open bottom can be used to isolate a broken nozzle so that surrounding flow can continue. The liquid in the unit cell with the broken nozzle can then be drained, the nozzle can be fixed, and the isolation chamber can be refilled and then removed to minimize disruption to the rest of the reactor.

Although atmospheric $CO_2$ can be used as a nutrient, supplemental $CO_2$ can optionally be provided. For example, sequestered, captured or produced $CO_2$ can be directed into the system and injected at the nozzle or another location.

The pumps can keep flow in the laminar flow regime or approximately in the laminar flow regime. In some cases, there can be functional limitations as well. For example, algae integrity may also limit the flows because the algae can break up or otherwise degrade in response to high shear flows which can be undesirable for growth stages. Similar considerations can apply to other microorganisms which are sensitive to high shear.

Though particularly suitable for algae the bioreactor unit can be used on all photosynthetic, chemotrophic, and autotropic microorganisms. Non-limiting examples of microorganisms can include *E. Coli*, dairy, yeast, aquaculture organisms, cell cultures, viruses, and the like.

The bioreactors system can comprise symmetrically shaped unit cells oriented in a two dimensional array. However, in some examples, the array can be extended into three-dimensions allowing for stacked arrays having hydrodynamically defined horizontal walls (i.e. floor and ceiling) between vertically spaced arrays of unit cells. For example, a second plurality of unit cells can be oriented above the plurality of unit cells which allows flow of the volume of liquid between the plurality of unit cells and the second plurality of unit cells. Corresponding injection ports can be aligned as previously described with each unit cell in these additional arrays. A second peripheral side wall can surround the second plurality of unit cells such that the volume of liquid is retained in the bioreactor. This second side wall can be a contiguous extension of the peripheral side wall of the first array or can be a separate wall, as long as fluid is retained within the bioreactor. Any number of stacked arrays can be used and in one example include from two to ten stacked arrays.

Bioreactors comprised of regular symmetric unit cells are highly scalable. The unit cells can have hexagonal symmetry, rectangular symmetry, square symmetry, or triangular symmetry. In addition, other tessellating structures could be used. Unlike other tessellated structures that have been used in bioreactors to date, which include material surfaces to define the tessellating cells, the bioreactors of the present technology can use only symmetry (without internal material walls) to define the unit cells. Regularly spaced flow nozzles in a symmetric pattern create the uniform unit cells that each operate similarly to an individual bioreactor.

Intermediate material boundaries are not present because of strategic placement of the flow nozzles and the dynamics of fluid flow created in an array of unit cells that have no material walls separating them. The system is scalable to very large scales that are industrially relevant (e.g., hundreds to thousands of acres) without loss of productivity. In this bioreactor system, productivity of one unit cell is substantially the same as the others. Typically, the lack of internal walls and material boundaries between unit cells can increase productivity and moderate energy input with larger reactor sizes. Further, tubular reactors can allow for improved photoexposure, however higher shear forces and friction are incurred due to higher reactor surface area.

Despite the lack of internal walls between unit cells, the plurality of unit cells can be surrounded by a peripheral side wall to retain liquid inside the bioreactor. The side wall can be the same height as the liquid height level or higher. In some examples, the side wall can be translucent to allow light to pass through. The side walls and the floor can be a single unitary piece, or the side walls can be separate pieces that are assembled with floor pieces to collectively form the bioreactor fluid containment structure. In some examples, unit cells at the edge of the reactor can have a combined floor and side wall piece, which includes both the floor of the unit cell and one or more side walls.

The bioreactor can also optionally be covered to reduce water loss due to evaporation, maintain more consistent temperatures inside the reactor (e.g., during winter), prevent disturbances in the surface flow due to high winds, and/or to retain carbon dioxide or other gases within an enclosed space between the fluid body and the cover and which is injected into the reactor to be used as a nutrient by the microorganisms. In the case of phototropic microorganisms, the covering can be transparent to allow sunlight, artificial light, or other suitable light source to pass through and expose the microorganisms. The covering can be at a height equal to the height of the liquid in the bioreactor, so that the liquid is in contact with the covering. Alternately, the covering can be above the surface of the liquid, so that a layer of air separates the liquid from the covering. A fully sealed system can retain $CO_2$, nitrates, phosphates, and water, and enhance growth. However, a cover that is in contact with the liquid can increase shear stress and attenuate photon flux, also affecting productivity. In addition, an air gap between the liquid and cover can allow condensation to form inside the cover, possibly reducing the amount of sunlight reaching the algae.

Algae require light for population growth and lipid production. Therefore, the bioreactor can be optimized to provide sunlight to the algae or other phototropic microorganisms. Photon penetration is also limited at high algae concentrations. The injection nozzles can create recirculating flow patterns that move the algae near the surface of the liquid to be exposed to sunlight. Depending on algae concentration, the most effective region for receiving sunlight can be only a few centimeters beneath the surface. The recirculating flow can also distribute nutrients to the algae. Nutrient transport includes minerals, $CO_2$, nitrogen, and other nutrients. Optimal algae growth can depend on dimensions of the unit cells, including width of the cell and height of the liquid in the cell, as well as the flow rate of liquid through the injection nozzle, and concentrations of $CO_2$ and other nutrients needed by the algae.

In some examples, optimal dimensions and flow rates can be calculated by using computational fluid dynamic models. Algae growth rates and consumption rates of nutrients can be measured and used to create additional models that can be used to design optimized bioreactors. Additional productivity can be achieved by modifying several factors including nozzle shape, pressure, diameter, and spacing; liquid pool height; algae strain, concentration, initial density, and initial size distribution; gas (e.g., $O_2$ and $CO_2$) mass fraction; nutrient (nitrogen and phosphorus) concentration and consumption kinetic constants; and photon flux and angle. Dimensionless groups (e.g., Re, Damkohler numbers for each nutrient, geometric ratios, inter alia) can be used to model processes in the bioreactor. Specific strains of algae can be better adapted to growth in the bioreactor, as well as producing a larger amount of lipids for production of biofuels and processing waste/process water. For example, algae strains that grow well in produced waters from mining and industrial processes can be used so that the bioreactor does not require large amounts of potable water to operate. Algae strains can also be selected to purify waste water. Computational fluid dynamics can be used to model the productivity, while experimentally determine missing parameters (e.g., kinetic constants). Evaporation ponds or 30 ft tanks can also be retrofitted with optimized bioreactors according to the present technology.

Because the unit cells simply number up to form the whole reactor, optimizing the performance of the unit cell optimizes the performance of the entire reactor. Several factors may influence reactor performance including unit cell dimensions (base length and liquid pool height) and geometry (square or hexagonal/triangular symmetry; these are the only close packed options); inlet and outlet port type (vertical nozzles, lateral nozzles, or perforated bottom plates) and location (e.g., nozzles or ports at the center or vertices of hexagons or squares); inlet and outlet flow rate and pressure; fluid properties (water viscosity and density); algae strain, concentration, density, size distribution, and growth rates; gas (e.g., $O_2$ and $CO_2$) mass fraction; nutrient (nitrogen and phosphorus) concentration and consumption rate constants; and photon flux and angle. The reactors presumably operate isothermally due to convective mixing, but heat transfer may be included as needed and may be available from the pumping and more importantly from the source of the water. For example, mining water or produced water is often heated when it enters the reactor.

Dimensionless groups can be obtained using the governing differential equations and the Buckingham Pi theorem with Rayleigh's method of indices as needed. Governing equations include Navier-Stokes, continuity for incompressible fluids, differential mass conservation for each nutrient species including $CO_2$, algae population balances, and photon conservation. Reactor fluid dynamics can be simulated using 3D computation fluid dynamics (CFD) simulations using commercially available software packages (COMSOL, fluent, etc.). The Reynolds number (Re) can be limited to laminar flow profiles to ensure scalability and minimize shear stresses on the algae. The flow of the algae can be modeled using the equations for slurries (albeit with much lower density than traditional slurries) at various volume fractions. Algae behave more like slurries than homogeneous mixtures in intensified processes where the algae concentration is particularly dense, the algae settle, and water usage is minimized. Photon density can be modeled as a function of position using Beer's law for adsorption (e.g., at 450 and 680 nm characteristic of chlorophyll) adjusted for variable algae density and Tyndal or Mie scatter to account for scattering based on data available in our laboratories. The concentration of $CO_2$ and the macronutrients, nitrogen and phosphorous, can be modeled using the equations of convective and diffusive mass transfer. Micronutrients (e.g. Ca, Mg, etc.) typically remain in excess in the wastewaters selected. The growth rate of algae and production of algal oils can be modeled using population balances that depend on the photon flux, $CO_2$, nitrogen and phosphorus. Rate constants for nutrient consumption can be determined from experimental data for algae. Such modeling can identify the good reactor dimensions and flow conditions to maximize algal oil production, while minimizing pumping power and material costs.

In some examples, the reactor can operate in chemostat/auxostat mode where culture media are continuously removed and refreshed. Nutrient recycling maximizes nutrient consumption. The reactor exit flow can contact a dialysis membrane with a high molecular weight cut off (e.g., ≥10 kDa) to ensure permeability to nutrients and waste products (if any) but not algae. In the opposite direction, a countercurrent stream containing waste water nutrients supplemented with nitrogen as necessary can flow in the countercurrent direction. The refreshed stream can return to the bioreactor via the pump. The contact area of the membrane, operated without pressure gradient to preserve stability, can meet or exceed the nutrient's required molar flow rate divided by its diffusive flux. The membrane permeability can be directly measured or derived from the manufacturer (Millipore, Pall, etc.). The recycle channel width can typically be no more than ⅓ of the largest nutrients diffusion length scale to ensure complete mixing of the nutrients prior to entering the reactor. Improved nutrient availability in chemostat mode can enhance algae growth rates, particularly at latter growth stages typically limited by nutrient availability.

Nutrient composition is one factor affecting growth. For example, when the nitrogen concentration is relatively high the algae increase in number. In contrast, when the nitrogen concentration level is low, the algae respond by increasing lipid concentrations. Sequenced patterns among multiple reactors can be used to vary conditions to optimize population growth versus lipid growth. In one example, four reactors (or sets of reactors) can be placed in operation. The first and optionally the second in the sequence can run nitrogen rich so that the number of cells grows quickly, while the third and fourth can run nitrogen poor so that the number of cells does not grow rapidly, but the amount of lipids contained therein does grow dramatically.

Additional examples of non-phototropic growth can include yeast and $E.\ coli$, both of which can make lipids or free fatty acids that can be then converted into biofuels. Photoheterotrophes can also be particularly advantageous in this regard taking in photons during the day and using chemical energy at night. The reactor is ideally suited to provide circulation to collect the photons during the day and measurably and selectively dose the microorganisms with chemicals in the evening. However, the bioreactor can also be used with nonphototropic species.

As mentioned previously, the bioreactors herein are readily scalable. Although other approaches can be used, in one example the following discussion outlines scaling design considerations, with a specific example of algae. The photon intensity varies as a function of the photobioreactor depth. If the algae are well mixed and sample (albeit stochastically) photons from the entire reactor volume and light enters only from the top, then the Beer-Lambert Law can be used to determine how the average photon intensity varies with reactor depth, H, and upper surface intensity, $I_0$. The Beer-Lambert Law is written as $$I(z) = I_o e^{-acz}, \qquad (1)$$

where I is the photon intensity at any position z, c is a concentration (assumed herein to be a molar concentration, though other options are possible) and a is a constant that has units corresponding to those selected for the concentration. The constant a can be determined from UV-vis data with A=acp, where A is the absorbance, p is path length of the spectrophotometer, and c can be determined from hemocytometry. This equation can be modified for integration in more than one spatial dimension, but to first order approximation, the photon intensity depends primarily on the depth given current geometry. The average intensity may be determined by integration $$\bar{I} = \frac{1}{\tau} \int_{t=0}^{t=\tau} \frac{1}{H} \int_{z=0}^{z=H} I_o e^{-acz} dz dt, \qquad (2)$$

where τ is the time over which the average is taken. In a laboratory environment, the photon intensity does not vary with time so the only averaging that remains necessary is averaging over the reactor depth. Integrating then gives $$\frac{\bar{I}}{I_o} = \frac{1 - e^{-acH}}{acH}, \tag{3}$$

If lighting does change with time, then the right hand side becomes the integrand of a time averaging integral because the concentration is time dependent. Although the growth rate varies with photon intensity, if we assert that the growth rate in the exponential phase depends on the average intensity $$\frac{dc}{dt} = k\bar{I}c. \tag{4}$$

This equation can include additional terms which accommodate death or nutrient concentrations. Michalis-Menton kinetics may also be appropriate. Then $$\frac{dc}{dt} = kI_o \frac{1 - e^{-acH}}{acH} c. \tag{5}$$

$$\ln \frac{(1 - e^{-acH})}{(1 - e^{-ac_{lag}H})} = kI_o(t - t_{lag}). \tag{6}$$

$$c = \frac{-1}{aH} \ln\left[1 - \left(1 - e^{-ac_{lag}H}\right)\text{Exp}[kI_o(t - t_{lag})]\right]. \tag{7}$$

From a production standpoint, the total biomass productivity per unit cell can be calculated. If m is the mass (or moles) of algae and s is the side of N hexagons then $$m = \frac{3\sqrt{3}}{2} Ns^2 Hc \frac{\pi}{6} \rho d_c^3 = \tag{8}$$

$$\frac{3\sqrt{3}}{2} \frac{Ns^2}{a} \frac{\pi}{6} \rho d_c^3 \ln\left[\frac{1}{1 - \left(1 - e^{-ac_{lag}H}\right)\text{Exp}[kI_o(t - t_{lag})]}\right].$$

where moles convert to mass via $4\pi d_c^3 \rho/3$.) This expression assumes that the algae is well mixed and does not hold when this assumption fails (e.g., at very low flow rates of the radial jet or where there is insufficient kinetic energy to lift the liquid). The number of hexagons is approximately equal to the total land area $A_{total}$ divided by the area of a given hexagon so $$N = \frac{2A_{total}}{3\sqrt{3} s^2}. \tag{9}$$

$$m = \frac{A_{total}}{a} \frac{\pi}{6} \rho d_c^3 \ln\left[\frac{1}{1 - \left(1 - e^{-ac_{lag}H}\right)\text{Exp}[kI_o(t - t_{lag})]}\right]. \tag{10}$$

The cell diameter is also assumed to not change substantially across time. Remarkably, this expression suggests that the biomass production is approximately linear in the depth.

The conditions that lead to the photobioreactor being well mixed can affect outcomes. There is a characteristic time for the liquid recycle process given by the ratio of the reactor volume to the volumetric flow rate $$\tau_{refill} = \frac{V}{Q} = \frac{6\sqrt{3}}{\pi} \frac{s^2 H}{d_j^2 U_o}, \tag{11}$$

where $d_j$ is the inner diameter of exiting tube and $U_o$ is the velocity of the same. A conical invicid jet impinging on a flat surface that then becomes a radial jet can be considered. See Poreh M, Y G Tsuei, and J E Cermak. 1967. "Investigation of a Turbulent Radial Wall Jet." Journal of Applied Mechanics June 1967: 457-463, which is incorporated herein by reference. The maximum velocity, $U_m$, of a radial invicid jet can be correlated as $$\frac{U_m b}{\sqrt{K}} = 1.32 \left(\frac{r}{b}\right)^{-1.1}, \tag{12}$$

where b is a characteristic distance between the pipe outlet and the floor, r is the radial distance from pipe outlet along the floor (although r+b can also be used), and $$K = \frac{\pi}{4} d_j^2 U_o^2. \tag{13}$$

We want to know the maximum velocity at the furthest point away from the center of the hexagon so we let r=s and set $b=h_o$ where $h_o$ is the exact distance between the pipe outlet and the floor. Then $$\frac{U_m h_o}{\sqrt{K}} = 1.32 \left(\frac{s}{h_o}\right)^{-1.1}. \tag{14}$$

Sufficient kinetic energy can be used in the radial jet to lift that packet of fluid to the upper surface of the tank with a safety factor of f>1. This factor can be strictly greater than one so that there is enough momentum for the fluid to turn over to the center of the unit cell once it reaches the top. Then $$\rho \Delta V g H f \leq \frac{1}{2} \rho V \bar{v}^2 \tag{15}$$

Average and maximum velocities can be related by $\bar{v}=U_m/2$, then $$\frac{32 f}{1.32^2 \pi} \leq \frac{d_j^2 U_o^2 h_o^{0.2}}{g H s^{2.2}}. \tag{16}$$

With a selected safety factor, internal pipe diameter, and distance between the pipe outlet and the floor plate, one can optimize or specify $U_o$, H and s. H can be optimized to insure at least the same average intensity as in lab experiments, recognizing that $I_o$ can be increased as necessary or that it will increase because the sun is brighter than internal lighting. The recycle/refill time can be constrained to be at least the same recycle/refill time as previously measured. Pumping energy and losses can also be estimated by accounting for floor and wall friction using known correlations.

The features of the bioreactor unit described above and exemplary embodiments are shown in the accompanying figures. It should be noted that the figures are schematics illustrating structural features of the bioreactor unit, and are not intended to convey scale. Furthermore, the exemplified figures are merely examples of how the bioreactor can be designed. Those skilled in the art can modify the structure after considering the present disclosure.

Example 1

A prototype reactor was designed including a seven-cell reactor with no internal walls to minimize internal shear filled with water. Several microalgae strain including the cyanobacterium *Synechococcus elongatus, Chaetoceros muelleri, Amphora coffeaeformis, Chaetoceros gracilis,* USU80 (green algae isolated from the Great Salt Lake), *Neochloris oleoabundans, Chlorealla sorokiniana,* and *Phaeodactylum tricornutum*—including diatoms and green algae were selected for this effort because of their ability to grow in mining waste water and Great Salt Lake brine and because of their track record in producing lipids for transportation fuels, can be grown separately for 14-21 days.

The algae are grown in mining produced water and municipal waste. *Chaetoceros muelleri* is grown in produced water from the Anadarko reinjection site in eastern Utah. The $CO_2$ can be from flue gas derived from a coal fired plant with or without dilution. Productivity of the bioreactor can be assessed by removing aliquots of algae (~250-400 mL) from the center and edge of the reactor to evaluate its performance. These samples can be accessed for algal density measured via optical density, algae size using microscopy with MATLAB image analysis and steric mode asymmetric flow field flow fractionation (AFFFF), cellular lipid volume fraction using confocal microscopy with volumetric image reconstruction of Nile Red lipid staining, total N and total P using a Lachat quikchem 8500 analyzer (Lachat, Loveland, Colo.), other elements by inductively coupled plasma (ICP) analysis, and $CO_2$ based on infrared sensors, pH, or gas chromatography (GC). The quality of the algal biomass was also assessed by determining the fraction of biomass that could be used for energy production. Although initially demonstrated for algae (proof-of-principle), the strategy is applicable to all photosynthetic, chemotrophic, and autotropic microorganisms.

Example 2

Bioreactors having hexagonal unit cells were constructed having 1, 7 and 19 unit cells. The 7 and 19 unit cell bioreactors were arranged as illustrated generally in FIGS. 4 and 16, except supply and return lines were introduced from above. Each unit cell was 18 inches high, 9 inches wide, and have wall thickness of ¼ inch. The bioreactors were filled to about 15 inches depth with a starter algae solution having 16.1 transmittance. The three bioreactors had a bioreactor volume of 13.1 L, 347.1 L, and 942.2 L, respectively. Volumes of 1.4 L, 9.8 L, and 26.4 L of starter algae solution was introduced into each of the three bioreactors, respectively. Miracle Grow® was used as the nutrient in each reactor in amounts of 19.8 gm, 138.9 gm, and 376.96 gm, respectively. Thus, the ratio of algae, nutrients, water and lighting were uniform across all three reactors. A circulation flow rate of 24 L/min and approximately 80° F. (+/−2° F.) liquid temperature was maintained throughout the experiment.

Figure 18:
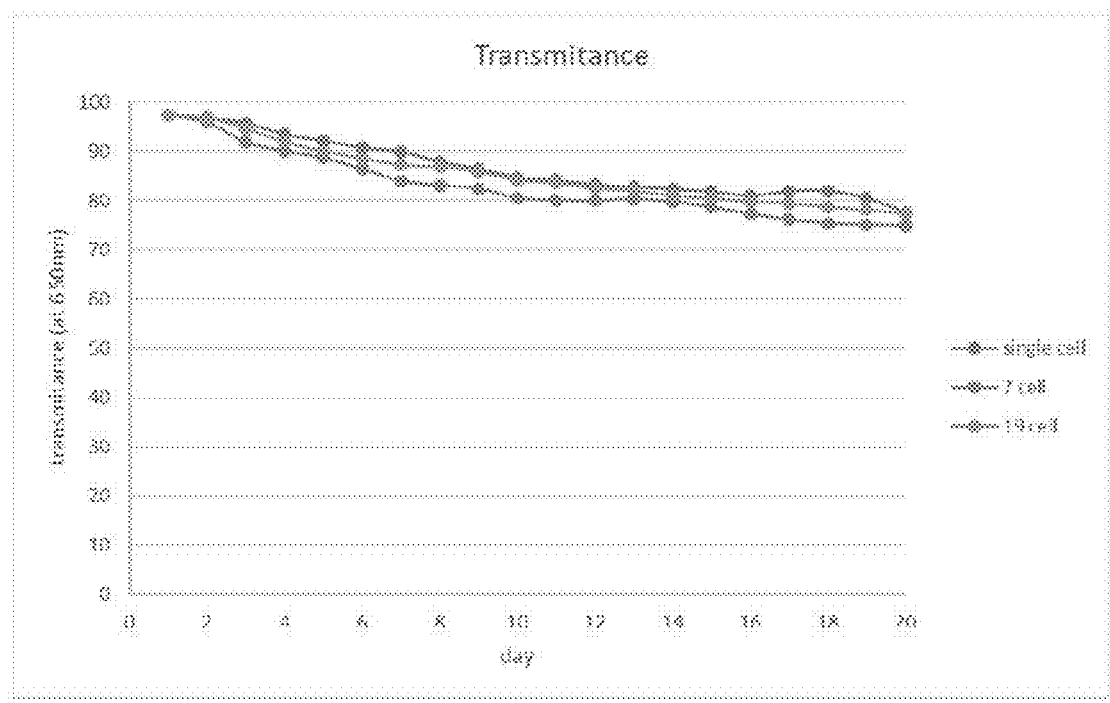
FIG. 18 is a graph of transmittance versus time for three different bioreactors in accordance with examples of the present technology.
Figure 19:
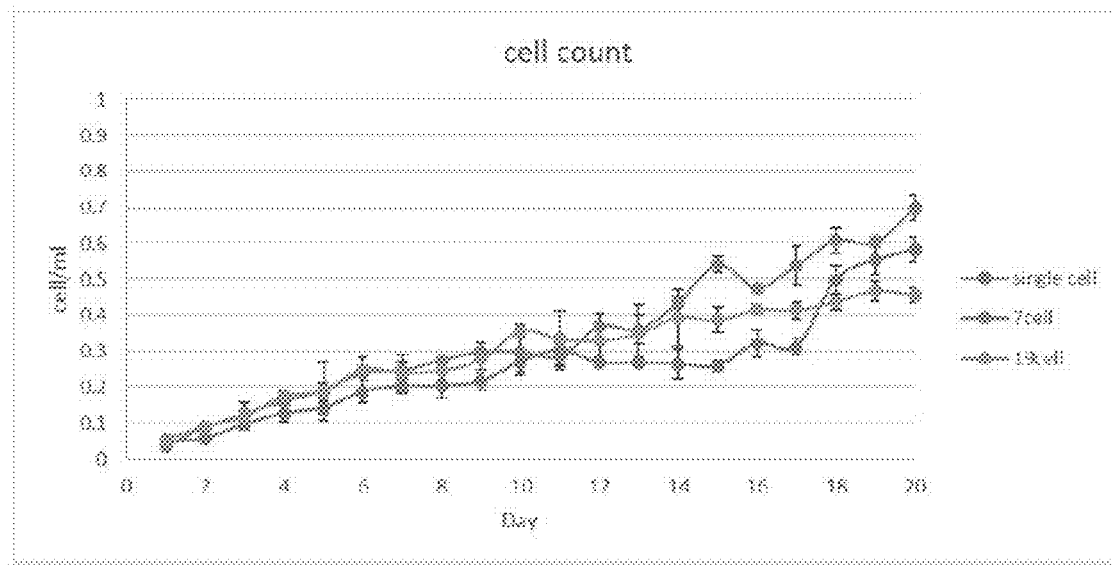
FIG. 19 is a graph of cell count versus time for three different bioreactors in accordance with examples of the present technology.
Figure 20:
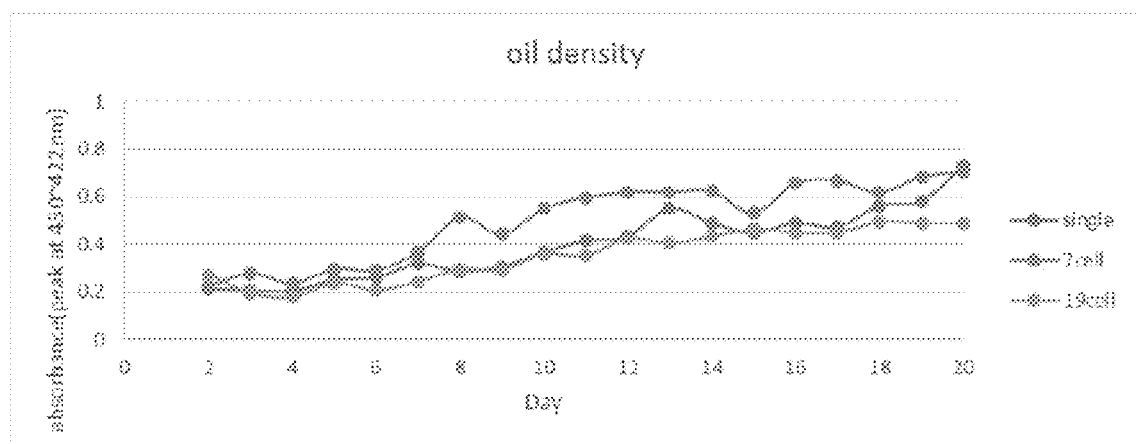
FIG. 20 is a graph of oil density versus time for three different bioreactors in accordance with examples of the present technology.

Transmittance, cell count and oil density data were collected regularly over 20 days. FIG. 18 illustrates progressive decrease in transmittance over time which is indicative of algal growth. FIG. 19 shows a progressive increase of cell count over time which also indicates relatively constant growth. FIG. 20 also evidences algal growth by a showing of progressive increase in oil density as a function of time.

The described features, structures, or characteristics may be combined in any suitable manner in one or more examples. In the preceding description numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A bioreactor comprising:
   a) a plurality of unit cells, wherein each unit cell comprises:
      i) a floor configured to support a volume of liquid, the floor being symmetric across at least one axis of symmetry; and
      ii) an injection port oriented at a center point of the at least one axis of symmetry and configured to inject a fluid into the volume of liquid, wherein the injection port comprises an injection nozzle that includes a fluid intake adjacent to a base of the injection nozzle,
   wherein the plurality of unit cells is substantially free of internal walls; and
   b) a peripheral side wall surrounding the plurality of unit cells such that the volume of liquid is retained in the bioreactor.

2. The bioreactor of claim 1, wherein the plurality of unit cells are formed as hexagons, rectangles, or triangles.

3. The bioreactor of claim 2, wherein the plurality of unit cells are formed as hexagons.

4. The bioreactor of claim 1, wherein the floor is a continuous floor piece shared by all of the plurality of unit cells.

5. The bioreactor of claim 1, wherein the floor is a unit floor piece corresponding to a single unit cell.

6. The bioreactor of claim 5, wherein the unit floor piece is configured to attach to adjacent unit floor pieces with a water-tight seal.

7. The bioreactor of claim 1, wherein the injection nozzle includes fluid jets that vertically circulate a fluid, nutrients, or microorganism within the unit cell.

8. The bioreactor of claim 1, wherein the injection nozzle is separately controlled by a mass flow controller.

9. The bioreactor of claim 1, further comprising a deflection baffle oriented about the base of the injection nozzle and spaced from the floor, such that the fluid intake is obscured by the deflection baffle when viewed from an aerial top view.

10. The bioreactor of claim 1, further comprising a pump configured to recirculate fluid from the fluid intake to the injection nozzle.

11. The bioreactor of claim 10, wherein the pump is a centrifugal pump.

12. The bioreactor of claim 1, wherein the injection port is adapted to inject the fluid within the volume of liquid from a top or a bottom of the at least one axis of symmetry.

13. The bioreactor of claim 1, further comprising the volume of liquid as an aqueous population of heterotropic microorganisms.

14. The bioreactor of claim 1, further comprising the volume of liquid as an aqueous algal population.

15. The bioreactor of claim 1, wherein the injection nozzle has a fluid outlet oriented at a nozzle height of 0.2% to 99.8% a wall height of the peripheral side wall.

16. The bioreactor of claim 1, wherein the peripheral side wall is translucent.

17. A method of cultivating a microorganism population:
    filling the bioreactor of claim 1 with the volume of liquid; and
    circulating the volume of liquid through the injection ports at flow rates sufficient to form the unit cells.

* * * * *

UNITED STATES PATENT AND TRADEMARK OFFICE
CERTIFICATE OF CORRECTION

PATENT NO.       : 9,790,459 B2
APPLICATION NO.  : 14/625470
DATED            : October 17, 2017
INVENTOR(S)      : Leanard Franklin Pease, III et al.

Page 1 of 1

It is certified that error appears in the above-identified patent and that said Letters Patent is hereby corrected as shown below:

On the Title Page

Item (72), Line 4. "McLeenan" should be --McLennan--.

Signed and Sealed this
Twenty-seventh Day of March, 2018

Andrei Iancu
*Director of the United States Patent and Trademark Office*